(12) United States Patent
Flaumenhaft et al.

(10) Patent No.: US 10,064,853 B2
(45) Date of Patent: Sep. 4, 2018

(54) COMPOUNDS FOR USE IN METHODS FOR TREATING DISEASES OR CONDITIONS MEDIATED BY PROTEIN DISULFIDE ISOMERASE

(71) Applicants: Beth Israel Deaconess Medical Center, Inc., Boston, MA (US); The Broad Institute, Inc.

(72) Inventors: Robert Flaumenhaft, Newton, MA (US); Partha Pratim Nag, Somerville, MA (US); Tatiana Pilyugina, Waltham, MA (US); Jun Pu, Shrewsbury, MA (US); Sivaraman Dandapani, Malden, MA (US); Benito Munoz, Newtonville, MA (US); Chris Dockendorff, Arlington, MA (US)

(73) Assignees: Beth Israel Deaconess Medical Center, Inc., Boston, MA (US); The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 15/632,809

(22) Filed: Jun. 26, 2017

(65) Prior Publication Data
US 2017/0304283 A1    Oct. 26, 2017

Related U.S. Application Data

(62) Division of application No. 14/899,180, filed as application No. PCT/US2014/043467 on Jun. 20, 2014, now abandoned.

(60) Provisional application No. 61/837,820, filed on Jun. 21, 2013.

(51) Int. Cl.
*A61K 31/445* (2006.01)
*A61K 31/454* (2006.01)

(52) U.S. Cl.
CPC .......... *A61K 31/445* (2013.01); *A61K 31/454* (2013.01)

(58) Field of Classification Search
CPC .................................................. A61K 31/445
See application file for complete search history.

(56) References Cited

FOREIGN PATENT DOCUMENTS

WO    WO-98/39315 A1    9/1998
WO    WO-98/51297 A1    11/1998

OTHER PUBLICATIONS

"ICD-9-CM Tabular List of Diseases (FY03)" on the Washington University School of Medicine in St. Louis website Online "http://gamma.wustl.edu/division/icd9tbp.pdf" accessed Sep. 10, 2015.*

Bekendam, "Inhibition of Protein Disulfide Isomerase in Thrombosis" Basic & Clinical Pharmacology & Toxicology, 2016, 119, 42-48.*
Flaumenhaft "Therapeutic Implications of Protein Disulfide Isomerase Inhibition in Thrombotic Disease" Arteriosclerosis, Thrombosis, and Vascular Biology (2015), 35(1), 16-23.*
Simone, Oncology: Introduction, Cecil Textbook of Medicine, 20th Edition, 1996 vol. 1, pp. 1004-1010.*
Howington "Treatment of Stage I and II Non-small Cell Lung Cancer Diagnosis and Management of Lung Cancer, 3rd ed: American College of Chest Physicians Evidence-Based Clinical Practice Guidelines" CHEST 2013; 143(5)(Suppl):e278S-e313S.*
Socinski "Treatment of Stage IV Non-small Cell Lung Cancer Diagnosis and Management of Lung Cancer, 3rd ed: American College of Chest Physicians Evidence-Based Clinical Practice Guideline" CHEST 2013; 143(5)(Suppl):e341S-e368S.*
Jett Treatment of Small Cell Lung Cancer Diagnosis and Management of Lung Cancer, 3rd ed: American College of Chest Physicians Evidence-Based Clinical Practice Guidelines CHEST 2013; 143(5)(Suppl):e400S-e419S.*
Sanz-Garcia, "Current and advancing treatments for metastatic colorectal cancer" Expert Opinion on Biological Therapy, 16:1, 2016 , 93-110.*
Garson "Models of ovarian cancer—Are we there yet?" Molecular and Cellular Endocrinology 239 (2005) 15-26.*
Sale "Models of ovarian cancer metastasis: Murine models" Drug Discovery Today: Disease Models 2006, 3, 150-154.*
Schober "New Advances in the Treatment of Metastatic Pancreatic Cancer" Digestion 2015;92:175-184.*
Boniface "Multidisciplinary management for esophageal and gastric cancer" Cancer Management and Research 2016:8 39-44.*
Gerratana "Do platinum salts fit all triple negative breast cancers?" Cancer Treatment Reviews 48 (2016) 34-41.*
Yoo "New drugs in prostate cancer" Prostate Int 4 (2016) 37-42.*

(Continued)

*Primary Examiner* — David K O'Dell
(74) *Attorney, Agent, or Firm* — McCarter & English, LLP

(57) ABSTRACT

The invention provides compounds of formula (I) that inhibit PDI, for use in methods to treat or prevent a disease or condition in a subject that would benefit by inhibition of PDI. Formula (I)

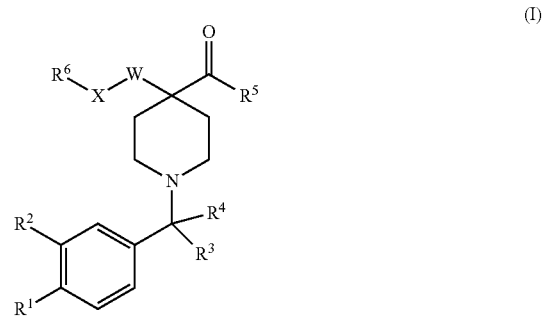

18 Claims, 2 Drawing Sheets

(56) References Cited

OTHER PUBLICATIONS

Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Ledford "US cancer institute overhauls cell lines" Nature Feb. 25, 2016 vol. 530 p. 391.*
Chaichian "Targeted Therapies in Systemic Lupus Erythematosus: A State-of-the-Art Review" J Clin Cell Immunol 2013, S6, 1-8.*
A.M. Bendele "Animal models of rheumatoid arthritis" J Musculoskel Neuron Interact 2001; 1(4):377-385.*
Bendele, "Animal Models of Arthritis: Relevance to Human Disease" Toxicol Pathol 1999 27: 134-142.*
Healthline Online "http://www.healthline.com/health/inflammatory-bowel-disease", accessed Sep. 9, 2015.*
Muller and Kräusslich in "Antiviral Strategies" Handbook of Experimental Pharmacology vol. 189 Chapter 1, pp. 1-24.*
Gao et al., "Synthesis of radiolabeled protein disulfide isomerase (PDI) inhibitors as new potential PET agents for imaging of the enzyme PDI in neurological disorders and cancer", *Applied Radiation and Isotopes*, 74:61-69, 2013.
Jasuja et al., "Protein disulfide isomerase inhibitors constitute a new class of antithrombotic agents", *Journal of Clinical Investigation*, 122(6):2104-2113, 2012.
Khan et al., "Discovery of a Small Molecule PDI Inhibitor That Inhibits Reduction of HIV-1 Envelope Glycoprotein gp120", *ACS Chemical Biology*, 6(3):245-251, 2011.
Database Registry [Online] Chemical Abstracts Service, Columbia, Ohio, US; Nov. 4, 2008, XP002729425, retrieved from STN Database accession No. 1070758-13-2.
Database Registry [Online] Chemical Abstracts Service, Columbia, Ohio, US; Oct. 27, 2008, XP002729426, retrieved from STN Database accession No. 1066996-75-2.

\* cited by examiner

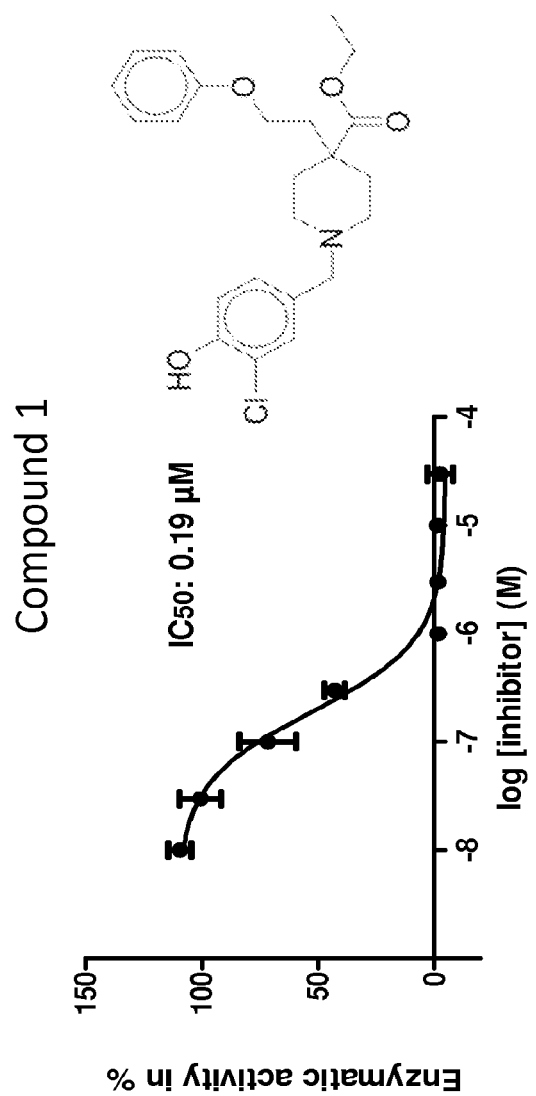
Figure 1. Inhibition of PDI by Compound 1 as monitored in an insulin reductase assay.

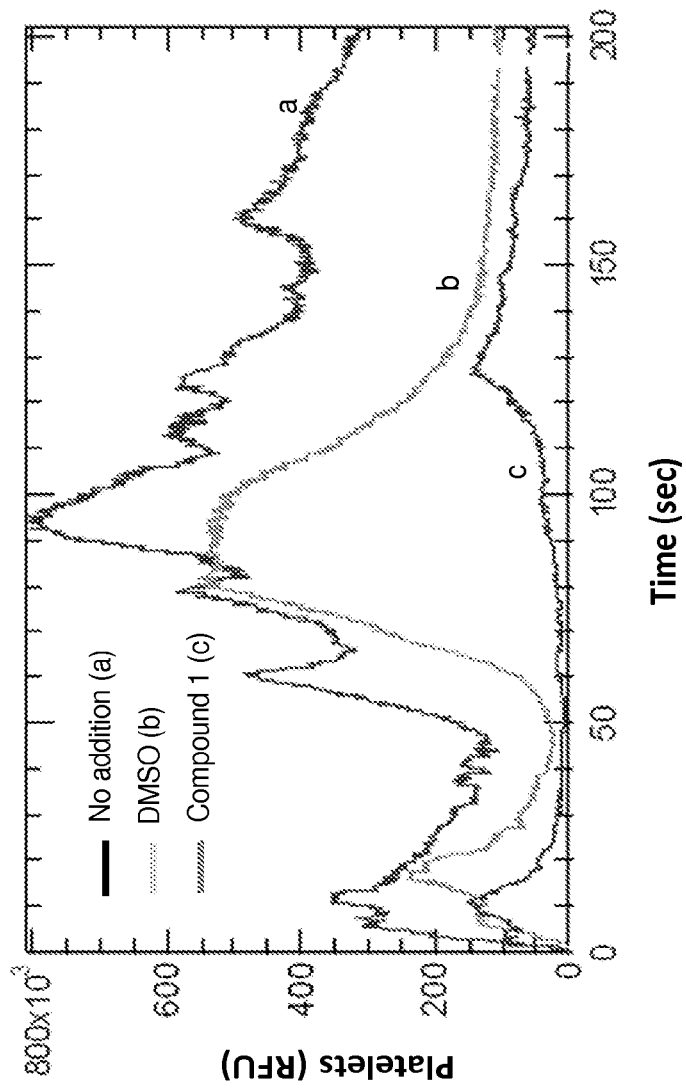
Figure 2. Compound 1 inhibits thrombus formation in vivo. Infusion of Compound 1 blocks platelet accumulation that occurs during thrombus formation induced by laser injury of cremaster arterioles in mice.

COMPOUNDS FOR USE IN METHODS FOR TREATING DISEASES OR CONDITIONS MEDIATED BY PROTEIN DISULFIDE ISOMERASE

RELATED APPLICATIONS

This application is a divisional application of U.S. patent application Ser. No. 14/899,180, filed Dec. 17, 2015, which is a 35 U.S.C. § 371 national stage filing of International Application No. PCT/US2014/043467, filed Jun. 20, 2014, which claims the benefit of U.S. Provisional Application No. 61/837,820, filed Jun. 21, 2013, the entire teachings of which are incorporated herein by reference.

STATEMENT REGARDING FEDERALLY SPONSORED RESEARCH OR DEVELOPMENT

This invention was made with government support under Grant No. DA032476, and HL112302 awarded by the National Institutes of Health. The government has certain rights in the invention.

BACKGROUND OF THE INVENTION

Arterial thrombosis causes heart attacks and strokes and is the leading cause of morbidity and mortality in the United States. Recurrent thrombosis is common despite current therapies.

Protein disulfide isomerase (PDI) is a member of an extended family of oxidoreductases, best known as endoplasmic reticulum-resident enzymes. These enzymes catalyze posttranslational disulfide bond formation and exchange and serve as chaperones during protein folding (Hatahet et al. *Antioxid Redox Signal.* 2009, 11(11), 2807-2850). PDI has been identified at many diverse subcellular locations outside the endoplasmic reticulum. It has biological functions on the cell surfaces of lymphocytes, hepatocytes, platelets, and endothelial cells (Manickam et al., *Br J Haematol,* 2008, 140(2), 223-229; Hotchkiss et al., *Biochim Biophys Acta.* 1998, 1388(2), 478-488; Essex et al., *Br J. Haematol.* 1999, 104(3), 448-454; Burgess et al., *J. Biol Chem.* 2000, 275(13), 9758-9766; Bennett et al., *J. Immunol.* 2000, 164(8), 4120-4129). PDI is rapidly secreted from both endothelial cells and platelets during thrombus formation in vivo (Cho et al., *J. Clin Invest.* 2008, 118(3), 1123-1131; Jasuja et al., *Blood* 2010, 116(22), 4665-4674). Inhibition of PDI using neutralizing antibodies blocks thrombus formation in several thrombosis models (Bennett et al., *J. Immunol.* 2000, 164(8), 4120-4129; Cho et al., *J. Clin Invest.* 2008, 118(3), 1123-1131; Jasuja et al., *Blood* 2010, 116(22), 4665-4674; Reinhardt et al.; *J. Clin Invest.* 2008, 118(3), 1110-1122). Inhibition of PDI in these models abrogates not only platelet accumulation at the injury site but also fibrin generation. These observations demonstrate a critical role for extracellular PDI in the initiation of thrombus formation. While currently available antithrombotic agents inhibit either platelet aggregation or fibrin generation, inhibition of secreted PDI blocks the earliest stages of thrombus formation, suppressing both pathways and indicating that PDI could be a useful target in the pharmacological control of thrombus formation. However, potential complications of inhibiting PDI are the ubiquitous distribution and critical function of intracellular PDI. Presently, available inhibitors of PDI are sulfhydryl-reactive compounds that bind covalently and are non-selective, acting broadly on thiol isomerases (Karala et al., *FEBS J.* 2010, 277(11), 2454-2462) or are cytotoxic (Lovat et al. *Cancer Res.* 2008, 68(13), 5363-5369; Khan et al. *ACS Chem. Biol.* 2011, 6(3), 245-251). Thus, there is a clear need for new approaches and new targets in the prevention and treatment of arterial thrombosis, such as new agents that interfere with PDI activity but are otherwise selective and well tolerated in therapeutic contexts.

SUMMARY OF THE INVENTION

In one aspect, the invention provides a compound of Formula (I):

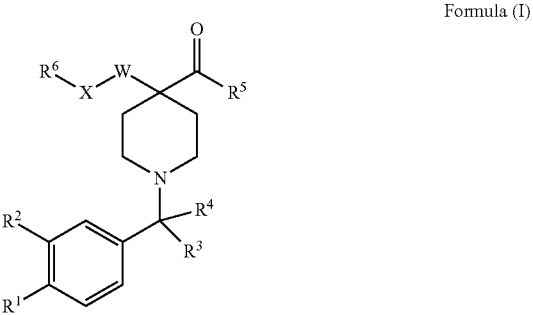

Formula (I)

or a pharmaceutically acceptable salt and/or prodrug thereof, wherein:
$R^1$ is selected from OH, acyloxy or a moiety capable of being hydrolyzed or otherwise metabolized under physiological conditions to a hydroxyl substituent (preferably OH);
$R^2$ is selected from H, lower alkyl, or halogen;
$R^3$ and $R^4$ are independently selected from H, F, and alkyl, or taken together with the carbon atom to which they are attached form a carbonyl group or a substituted or unsubstituted 3-7 membered cycloalkyl ring;
$R^5$ is selected from $OR^7$, $NHR^7$, and $NR^7R^8$, wherein $R^7$ and $R^8$ are each independently selected from H and substituted or unsubstituted alkyl, aryl, aralkyl, cycloalkyl, and cycloalkylalkyl, or taken together with the nitrogen atom to which they are attached form a substituted or unsubstituted 3-7 membered heterocyclyl ring (e.g., a pyrrolidine, piperidine, morpholine, or piperazine ring) (preferably $OR^7$, wherein $R^7$ is substituted or unsubstituted alkyl);
W represents a $C_1$-$C_3$ alkylene group, preferably ethylene;
X is selected from O, S, and $NR^9$ (preferably O), wherein $R^9$ is selected from H or lower alkyl; and
$R^6$ is selected from substituted or unsubstituted aryl or heteroaryl, preferably substituted or unsubstituted aryl.

In certain embodiments, the following compounds are excluded from Formula I:

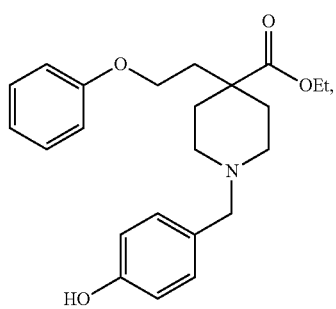

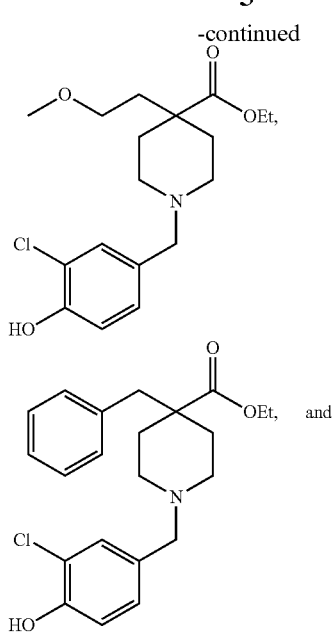
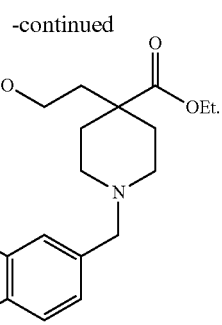
In certain embodiments, $R^2$ is H or halogen; preferably H or Cl.
In certain preferred embodiments, $R^3$ and $R^4$ are H, or, taken together with the carbon atom to which they are attached, form a carbonyl group.
In certain embodiments, the compound of Formula I is selected from:
| Compound No.# | Structure | PDI_Inhibition_ $IC_{50}$ (μM)† |
|---|---|---|
| 1 | 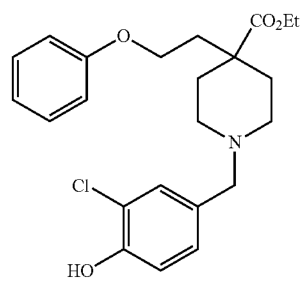 [SMILES: CCOC(=O)C1(CCOc2ccccc2)CCN(Cc2ccc(O)c(Cl)c2)CC1] | 0.25 |
| 4 | 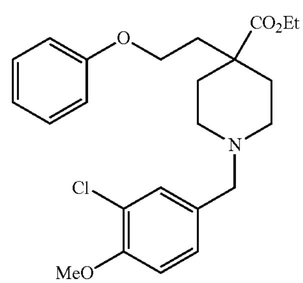 [SMILES: CCOC(=O)C1(CCOc2ccccc2)CCN(Cc2ccc(OC)c(Cl)c2)CC1] | >30 |
| 5 | 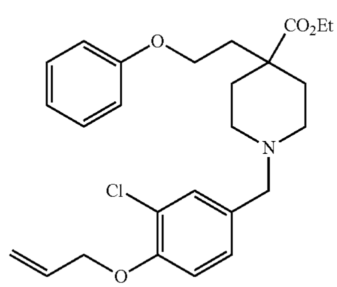 [SMILES: C=CCOc1ccc(CN2CCC(CCOc3ccccc3)(C(=O)OCC)CC2)cc1Cl] | >30 |

-continued

| Compound No.# | Structure | PDI_Inhibition_ IC$_{50}$ (µM)† |
|---|---|---|
| 6 | 1-(4-methoxybenzyl)-4-(2-phenoxyethyl)piperidine-4-carboxylic acid ethyl ester | >30 |
| 8 | 1-((2-oxo-2,3-dihydrobenzo[d]oxazol-6-yl)methyl)-4-(2-phenoxyethyl)piperidine-4-carboxylic acid ethyl ester | >30 |
| 9 | 1-(3-chloro-4-hydroxybenzoyl)-4-(2-phenoxyethyl)piperidine-4-carboxylic acid ethyl ester | 2.25 |
| 13 | 1-(3-chloro-4-hydroxybenzyl)-4-(2-phenoxyethyl)piperidine-4-carboxylic acid isopropyl ester | 0.85 |
| 14 | 1-(3-chloro-4-hydroxybenzyl)-4-(2-phenoxyethyl)piperidine-4-carboxylic acid tert-butyl ester | 0.65 |

-continued

| Compound No.# | Structure | PDI_Inhibition_ IC$_{50}$ (μM)† |
|---|---|---|
| 15 | 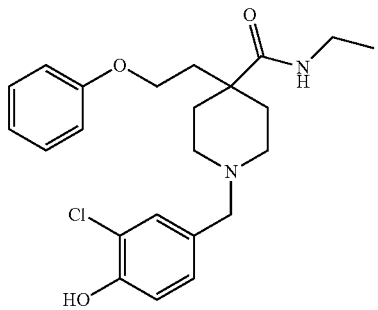 [SMILES: CCNC(=O)C1(CCOc2ccccc2)CCN(Cc2ccc(O)c(Cl)c2)CC1] | >30 |
| 16 | 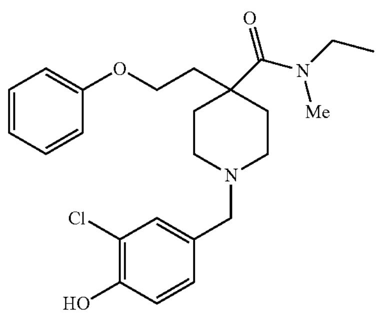 [SMILES: CCN(C)C(=O)C1(CCOc2ccccc2)CCN(Cc2ccc(O)c(Cl)c2)CC1] | 3.0 |
| 17 | 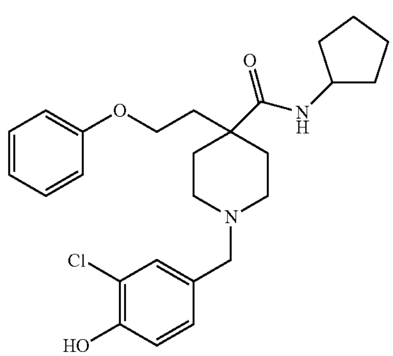 [SMILES: O=C(NC1CCCC1)C1(CCOc2ccccc2)CCN(Cc2ccc(O)c(Cl)c2)CC1] | 4.0 |
| 18 | 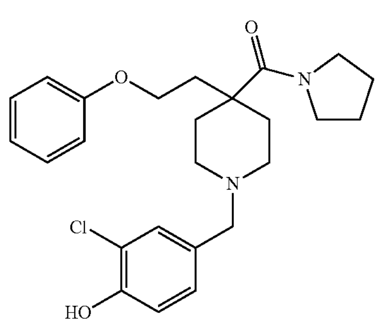 [SMILES: O=C(N1CCCC1)C1(CCOc2ccccc2)CCN(Cc2ccc(O)c(Cl)c2)CC1] | >30 |

-continued

| Compound No.# | Structure | PDI_Inhibition_ IC$_{50}$ (μM)† |
|---|---|---|
| 19 | 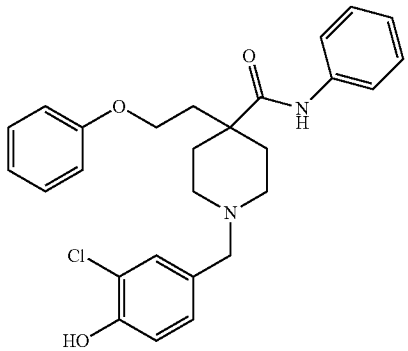 [SMILES: O=C(Nc1ccccc1)C1(CCOc2ccccc2)CCN(Cc2ccc(O)c(Cl)c2)CC1] | 22.5 |

In some preferred embodiments, the compound is selected from:

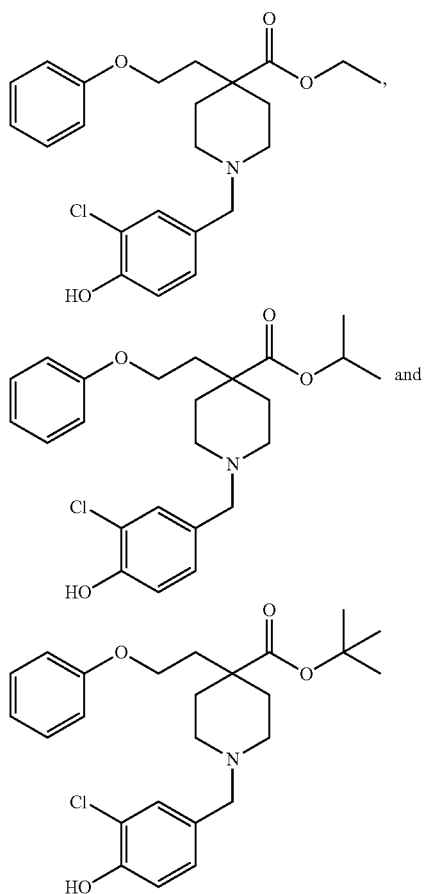

or a pharmaceutically acceptable salt and/or prodrug thereof.

In one aspect, the invention provides a pharmaceutical composition comprising a compound as disclosed herein and a pharmaceutically acceptable excipient or solvent. In certain embodiments, a pharmaceutical composition may comprise a prodrug of a compound as disclosed herein.

In another aspect, the invention provides a method of inhibiting protein disulfide isomerase in a patient, e.g., for treating or preventing a disease or condition mediated by protein disulfide isomerase, or for inhibiting a process mediated by protein disulfide isomerase, comprising administering to a patient a compound or composition as disclosed herein. In certain embodiments, the disease or condition is thrombosis, thrombotic diseases, infectious diseases including HIV, cancer or inflammation. In certain embodiments, the thrombotic disease is acute myocardial infarction, stable angina, unstable angina, aortocoronary bypass surgery, acute occlusion following coronary angioplasty and/or stent placement, transient ischemic attacks, cerebrovascular disease, peripheral vascular disease, placental insufficiency, prosthetic heart valves, atrial fibrillation, anticoagulation of tubing, deep vein thrombosis or pulmonary embolism. In certain embodiments, the infectious disease is HIV, dengue virus, rotavirus, chlamydia, cytoxicity of diphtheria toxin or phagocytosis of *Leishmania chagasi* promastigotes. In certain embodiments, the cancer is breast cancer or neuroblastoma. In certain embodiments, inflammation is inflammation of the lungs, joints, connective tissue, eyes, nose, bowel, kidney, liver, skin, central nervous system, vascular system and heart. Inflammatory lung conditions include, but are not limited to, asthma, adult respiratory distress syndrome, bronchitis, pulmonary inflammation, pulmonary fibrosis, and cystic fibrosis (which may additionally or alternatively involve the gastro-intestinal tract or other tissue(s)). Inflammatory joint conditions include rheumatoid arthritis, rheumatoid spondylitis, juvenile rheumatoid arthritis, osteoarthritis, gouty arthritis and other arthritic conditions. Eye diseases with an inflammatory component include, but are not limited to, uveitis (including iritis), conjunctivitis, scleritis, keratoconjunctivitis sicca, and retinal diseases, including, but not limited to, diabetic retinopathy, retinopathy of prematurity, retinitis pigmentosa, and dry and wet age-related macular degeneration. Inflammatory bowel conditions include Crohn's disease, ulcerative colitis and distal proctitis. Inflammatory skin diseases include, but are not limited to, conditions associated with cell proliferation, such as psoriasis, eczema and dermatitis, (e.g., eczematous dermatitides, topic and seborrheic dermatitis, allergic or irritant contact dermatitis, eczema craquelee, photoallergic dermatitis, phototoxic dermatitis, phytophotodermatitis, radiation dermatitis, and stasis dermatitis). Other inflammatory skin diseases include, but are not limited to, scleroderma, ulcers and erosions resulting from trauma, burns, bullous disorders, or ischemia of the skin or mucous membranes, several forms of ichthyoses, epidermolysis bullosae, hypertrophic scars, keloids, cutaneous changes of intrinsic aging, photoaging, frictional blistering caused by mechanical shearing of the skin and cutaneous atrophy resulting from the topical use of corticosteroids. Additional inflammatory skin conditions include inflammation of mucous membranes, such as cheilitis, chapped lips, nasal irritation, mucositis and vulvovaginitis. Inflammatory disorders of the endocrine system include, but are not limited to, autoimmune thyroiditis (Hashimoto's disease), Type I diabetes, and acute and chronic inflammation of the adrenal cortex. Inflammatory conditions of the cardiovascular system include, but are not limited to, coronary infarct damage, peripheral vascular disease, myocarditis, vasculitis, revascularization of stenosis, artherosclerosis, and vascular disease associated with Type II diabetes. Inflammatory condition of the kidney include, but are not limited to, glomerulonephritis, interstitial nephritis, lupus nephritis, nephritis secondary to Wegener's disease, acute renal failure secondary to acute nephritis, Goodpasture's syndrome, post-obstructive syndrome and tubular ischemia. Inflammatory conditions of the liver include, but are not limited to, hepatitis (arising from viral infection, autoimmune responses, drug treatments, toxins, environmental agents, or as a secondary consequence of a primary disorder), biliary atresia, primary biliary cirrhosis and primary sclerosing cholangitis. Inflammatory conditions of the central nervous system include, but are not limited to, multiple sclerosis and neurodegenerative diseases such as Alzheimer's disease, Parkinson's disease, or dementia associated with HIV infection. Other inflammatory conditions include periodontal disease, tissue necrosis in chronic inflammation, endotoxin shock, smooth muscle proliferation disorders, graft versus host disease, tissue damage following ischemia reperfusion injury, and tissue rejection following transplant surgery. In certain embodiments, the process is blood clotting, platelet aggregation or fibrin generation.

BRIEF DESCRIPTION OF THE FIGURES

FIG. 1 is a graph showing the percent inhibition of enzymatic activity in an insulin reductase assay for compound 1 versus the log of the concentration of the inhibitor.

FIG. 2 is a graph showing platelet accumulation that occurs during thrombus formation in vivo in the presence of DMSO, Compound 1, and with no compounds administered.

DETAILED DESCRIPTION OF THE INVENTION

The invention provides compounds that inhibit PDI, as well as methods to treat or prevent a disease or condition in a subject that would benefit by inhibition of PDI by administering such compounds.

I. Compounds

Compounds of the invention include compounds of Formula I as disclosed above and their salts (including pharmaceutically acceptable salts). Such compounds are suitable for the compositions and methods disclosed herein.

In some embodiments, the compound of Formula (I) is selected from the compounds in Table A:

TABLE A

| Compound No.[#] | Structure | PDI_Inhibition_ $IC_{50}$ (μM)[†] |
|---|---|---|
| 1 | [structure] | 0.25 |
| 4 | [structure] | >30 |

TABLE A-continued

| Compound No.# | Structure | PDI_Inhibition_ IC$_{50}$ (μM)† |
|---|---|---|
| 5 | 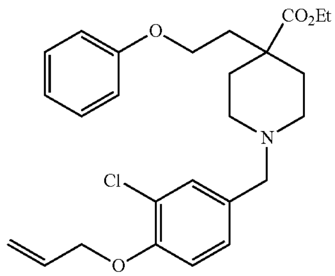 [SMILES: C=CCOc1ccc(CN2CCC(CCOc3ccccc3)(C(=O)OCC)CC2)cc1Cl] | >30 |
| 6 | 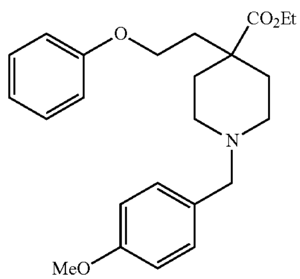 [SMILES: CCOC(=O)C1(CCOc2ccccc2)CCN(Cc2ccc(OC)cc2)CC1] | >30 |
| 8 | 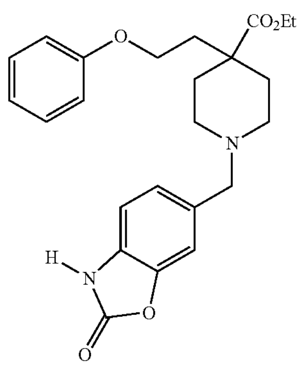 [SMILES: CCOC(=O)C1(CCOc2ccccc2)CCN(Cc2ccc3[nH]c(=O)oc3c2)CC1] | >30 |
| 9 | 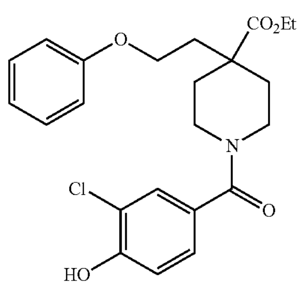 [SMILES: CCOC(=O)C1(CCOc2ccccc2)CCN(C(=O)c2ccc(O)c(Cl)c2)CC1] | 2.25 |
| 13 | 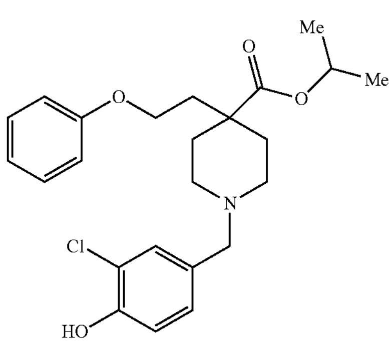 [SMILES: CC(C)OC(=O)C1(CCOc2ccccc2)CCN(Cc2ccc(O)c(Cl)c2)CC1] | 0.85 |

TABLE A-continued
| Compound No.# | Structure | PDI_Inhibition_ IC$_{50}$ (μM)† |
|---|---|---|
| 14 | 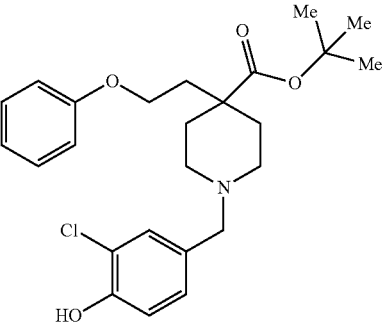 [SMILES: CC(C)(C)OC(=O)C1(CCOc2ccccc2)CCN(Cc2ccc(O)c(Cl)c2)CC1] | 0.65 |
| 15 | 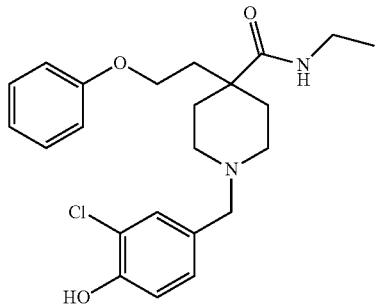 [SMILES: CCNC(=O)C1(CCOc2ccccc2)CCN(Cc2ccc(O)c(Cl)c2)CC1] | >30 |
| 16 | 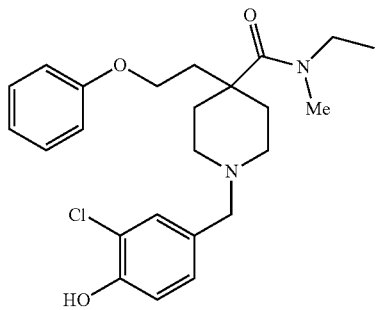 [SMILES: CCN(C)C(=O)C1(CCOc2ccccc2)CCN(Cc2ccc(O)c(Cl)c2)CC1] | 3.0 |
| 17 | 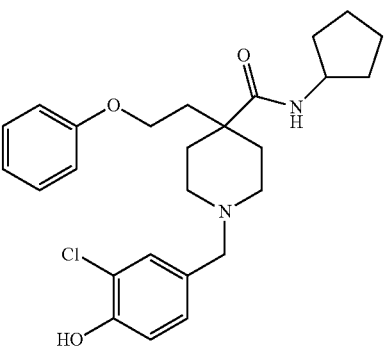 [SMILES: O=C(NC1CCCC1)C1(CCOc2ccccc2)CCN(Cc2ccc(O)c(Cl)c2)CC1] | 4.0 |
| 18 | 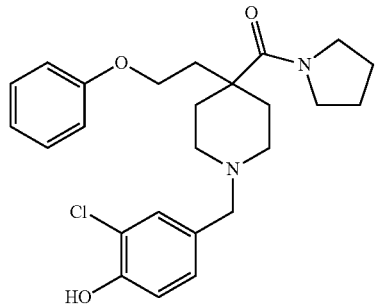 [SMILES: O=C(N1CCCC1)C1(CCOc2ccccc2)CCN(Cc2ccc(O)c(Cl)c2)CC1] | >30 |

TABLE A-continued

| Compound No.[#] | Structure | PDI_Inhibition_ IC$_{50}$ (µM)[†] |
|---|---|---|
| 19 | 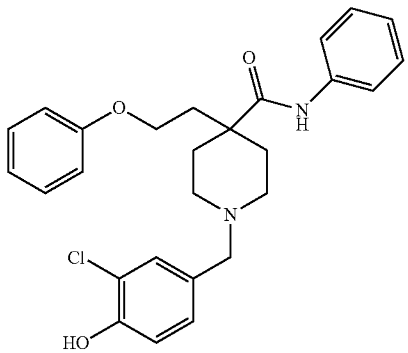 [SMILES: O=C(Nc1ccccc1)C1(CCOc2ccccc2)CCN(Cc2ccc(O)c(Cl)c2)CC1] | 22.5 |

[†]Average of two independent experiments

In some embodiments, the compound of Formula (I) is selected from the compounds in Table B:

| | | PDI_ Inhibition_ IC$_{50}$ (uM) | Counter Screen: Selectivity against other thiol isomerases IC$_{50}$ (µM) | | | |
|---|---|---|---|---|---|---|
| Compound No. | Structure | | ERp5* | Thioredoxin | Thioredoxin reductase | ERp57 |
| 1 | | 0.25 | >30 | >30 | >30 | >30 |
| 14 | | 0.65 | >30 | >30 | >30 | >30 |
| 13 | | 0.85 | >30 | >30 | >30 | >30 |

-continued

| Compound No. | Structure | PDI Inhibition IC$_{50}$ (uM) | Counter Screen: Selectivity against other thiol isomerases IC$_{50}$ (μM) | | | |
|---|---|---|---|---|---|---|
| | | | ERp5* | Thioredoxin | Thioredoxin reductase | ERp57 |
| 16 | 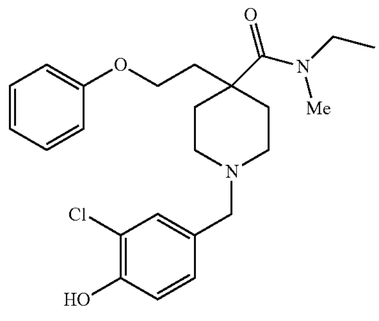 [SMILES: CCN(C)C(=O)C1(CCOc2ccccc2)CCN(Cc2ccc(O)c(Cl)c2)CC1] | 3.0 | N.D | >30 | >30 | >30 |
| 9 | 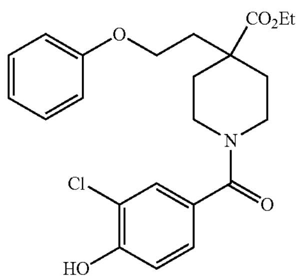 [SMILES: CCOC(=O)C1(CCOc2ccccc2)CCN(C(=O)c2ccc(O)c(Cl)c2)CC1] | 2.25 | N.D | >30 | >30 | >30 |
| 7 | 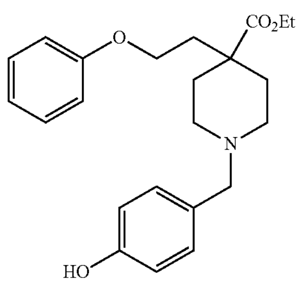 [SMILES: CCOC(=O)C1(CCOc2ccccc2)CCN(Cc2ccc(O)cc2)CC1] | 15.0 | N.D | >30 | >30 | >30 |
| 19 | 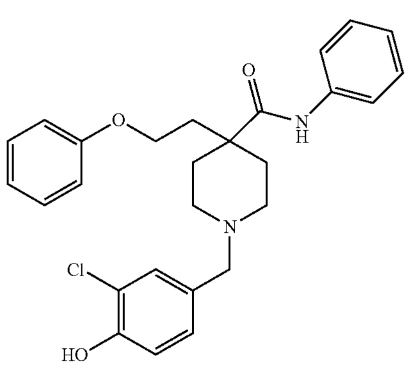 [SMILES: O=C(Nc1ccccc1)C1(CCOc2ccccc2)CCN(Cc2ccc(O)c(Cl)c2)CC1] | 22.5 | N.D | >30 | >30 | >30 |

-continued

| Compound No. | Structure | PDI Inhibition IC$_{50}$ (uM) | Counter Screen: Selectivity against other thiol isomerases IC$_{50}$ (μM) | | | |
|---|---|---|---|---|---|---|
| | | | ERp5* | Thioredoxin | Thioredoxin reductase | ERp57 |
| 17 | (structure) | 4.0 | N.D | >30 | >30 | >30 |
| 4 | (structure) | >30 | N.D | >30 | >30 | >30 |

*N.D: not determined.

II. Definitions

The term "alkoxy" refers to an oxygen having an alkyl group attached thereto. Representative alkoxy groups include methoxy, ethoxy, propoxy, isoproproxy, tert-butoxy and the like.

The terms "halogen", "halide" and "halo", as used herein, mean halogen and include fluoro, chloro, bromo and iodo.

The term "acyloxy" refers to means a straight-chain or branched alkanoyl group having 1 to 6 carbon atoms, such as formyl, acetyl, propanoyl, butyryl, valeryl, pivaloyl and hexanoyl, and arylcarbonyl group described below, or a heteroarylcarbonyl group described below. The aryl moiety of the arylcarbonyl group means a group having 6 to 16 carbon atoms such as phenyl, biphenyl, naphthyl, or pyrenyl. The heteroaryl moiety of the heteroarylcarbonyl group contains at least one hetero atom from O, N, and S, such as pyridyl, pyrimidyl, pyrroleyl, furyl, benzofuryl, thienyl, benzothienyl, imidazolyl, triazolyl, quinolyl, iso-quinolyl, benzoimidazolyl, thiazolyl, benzothiazolyl, oxazolyl, and indolyl.

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g. methyl, ethyl, n-propyl, i-propyl, n-butyl and n-pentyl.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety.

The term "$C_1$-$C_3$ alkylene" refers to a branched or unbranched, substituted or unsubstituted, hydrocarbon chain containing 1 to 3 carbon atoms) that connects two substituents, such as methylene, ethylene, propylene and trimethylene, most preferably ethylene.

The term "aliphatic", as used herein, includes straight, chained, branched or cyclic hydrocarbons which are completely saturated or contain one or more units of unsaturation. Aliphatic groups may be substituted or unsubstituted.

The terms "amine" and "amino" are art-recognized and refer to both unsubstituted and substituted amines and salts thereof, e.g., a moiety that can be represented by

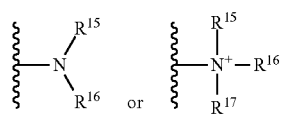

wherein $R^{15}$, $R^{16}$, and $R^{17}$ each independently represent a hydrogen or a hydrocarbyl group, or $R^{15}$ and $R^{16}$ taken together with the N atom to which they are attached complete a heterocycle having from 4 to 8 atoms in the ring structure.

The term "aryl", as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like.

The term "aralkyl", as used herein, refers to an alkyl group substituted with one or more aryl groups.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl.

The term "cycloalkylalkyl", as used herein, refers to an alkyl group substituted with one or more cycloalkyl groups.

The term "ester", as used herein, refers to a group —C(O)OR$^{17}$ wherein R$^{18}$ represents a hydrocarbyl group, such as an alkyl group or an aralkyl group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "heteroatom", as used herein, means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. Heterocyclyl groups include, for example, piperidine, piperazine, pyrrolidine, morpholine, lactones, lactams, and the like.

The term "C$_{x-y}$" when used in conjunction with a chemical moiety, such as, acyl, acyloxy, alkyl, alkenyl, alkynyl, or alkoxy is meant to include groups that contain from x to y carbons in the chain. For example, the term "C$_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. C$_0$ alkyl indicates a hydrogen where the group is in a terminal position, a bond if internal. The terms "C$_{2-y}$alkenyl" and "C$_{2-y}$alkynyl" refer to substituted or unsubstituted unsaturated aliphatic groups analogous in length and possible substitution to the alkyls described above, but that contain at least one double or triple bond respectively.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. Examples of straight chain or branched chain lower alkyl include methyl, ethyl, isopropyl, propyl, butyl, tertiary-butyl, and the like.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

Unless specifically stated as "unsubstituted," references to chemical moieties herein are understood to include substituted variants. For example, reference to an "alkyl" group or moiety implicitly includes both substituted and unsubstituted variants.

At various places in the present specification substituents of compounds of the invention are disclosed in groups or in ranges. It is specifically intended that the invention include each and every individual subcombination of the members of such groups and ranges. For example, the term "C$_1$-C$_6$ alkyl" is specifically intended to individually disclose methyl, ethyl, propyl, isopropyl, n-butyl, sec-butyl, isobutyl, etc.

For a number qualified by the term "about", a variance of 2%, 5%, 10% or even 20% is within the ambit of the qualified number.

The term "prodrug" is intended to encompass compounds which, under physiologic conditions, are converted into the therapeutically active agents of the present invention (e.g., a compound of Formula I). A common method for making a prodrug is to include one or more selected moieties which are hydrolyzed under physiologic conditions to reveal the desired molecule. In other embodiments, the prodrug is converted by an enzymatic activity of the host animal. For example, esters (e.g., esters of alcohols or carboxylic acids) are preferred prodrugs of the present invention. In various embodiments disclosed herein (e.g., the various compounds, compositions, and methods), some or all of the compound of Formula I can be replaced with a suitable prodrug, e.g., wherein a hydroxyl or carboxylic acid present in the parent compound is presented as an ester.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample when administered prior to manifestation of the disorder or condition.

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The phrase "conjoint administration" refers to any form of administration in combination of two or more different therapeutic compounds such that the second compound is administered while the previously administered therapeutic compound is still effective in the body (e.g., the two compounds are simultaneously effective in the patient). For example, the different therapeutic compounds can be administered either in the same formulation or in separate formulations, either concomitantly or sequentially.

III. Pharmaceutical Compositions

PDI inhibitors of the present invention may be provided in a pharmaceutical composition, e.g., combined with a pharmaceutically acceptable carrier, for administration to a patient. Such a composition may also contain diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. Such additional factors and/or agents may be included in the pharmaceutical composition to produce a synergistic effect with the PDI inhibitors.

The pharmaceutical compositions may be in the form of a liposome or micelles in which the PDI inhibitors are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The terms "pharmaceutically effective amount" or "therapeutically effective amount", as used herein, means the total amount of each active component of the pharmaceutical composition or method that is sufficient to show a meaningful patient benefit, e.g., treatment, healing, prevention, inhibition or amelioration of a physiological response or condition, such as an inflammatory condition or pain, or an increase in rate of treatment, healing, prevention, inhibition or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

Each of the methods or uses of the present invention, as described herein, comprises administering to a mammal in need of such treatment or use a pharmaceutically or therapeutically effective amount of PDI inhibitors, or a pharmaceutically acceptable salt or prodrug form thereof.

Administration of PDI inhibitors used in the pharmaceutical composition or to practice the methods of the present invention can be carried out in a variety of conventional ways, such as oral ingestion, inhalation, or cutaneous, subcutaneous, or intravenous, intramuscular, and intraperitoneal injection.

When a therapeutically effective amount of a PDI inhibitor (s) is administered orally, the compound(s) of the present invention may be in the form of a tablet, capsule, powder, solution or elixir. When administered in tablet form, the pharmaceutical composition may additionally contain a solid carrier such as a gelatin or an adjuvant. The tablet, capsule, and powder may contain from about 5 to 95% of a PDI inhibitor, and preferably from about 10% to 90% of a PDI inhibitors. When administered in liquid form, a liquid carrier such as water, petroleum, oils of animal or plant origin such as peanut oil, mineral oils, phospholipids, tweens, triglycerides, including medium chain triglycerides, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition typically contains from about 0.5 to 90% by weight of a PDI inhibitor, and preferably from about 1 to 50% by weight of a PDI inhibitor.

When a therapeutically effective amount of a PDI inhibitor(s) is administered by intravenous, cutaneous or subcutaneous injection, such compound(s) may be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the PDI inhibitors an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the PDI inhibitor may also contain stabilizers, preservatives, buffers, antioxidants, or other additives known to those of skill in the art.

The amount of the PDI inhibitor(s) in the pharmaceutical composition will depend upon the nature and severity of the disease or condition, and on the nature of prior treatments the patient has undergone. Ultimately, the practitioner will decide the amount of the PDI inhibitor with which to treat each individual patient. Initially, the practitioner may administer low doses of the PDI inhibitor and observe the patient's response. Larger doses of compounds of the PDI inhibitor may be administered until the optimal therapeutic effect is obtained for the patient, and at that point the dosage is not increased further. Representative doses of the present invention include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during one day, especially when relatively large amounts are deemed to be needed. It is contemplated that the various pharmaceutical compositions used to practice the methods of the present invention should contain about 0.1 μg to about 100 mg (preferably about 0.1 mg to about 50 mg, more preferably about 1 mg to about 2 mg) of PDI inhibitor per kg body weight.

IV. Synthetic Preparation

The compounds disclosed herein can be prepared in a variety of ways known to one skilled in the art of organic synthesis, and in analogy with the exemplary compounds whose synthesis is described herein. The starting materials used in preparing these compounds may be commercially available or prepared by known methods. Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis*, 44th. Ed., Wiley & Sons, 2006, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

V. Exemplification

The invention now being generally described, it will be more readily understood by reference to the following examples which are included merely for purposes of illustration of certain aspects and embodiments of the present invention, and are not intended to limit the invention.

All reagents and solvents were purchased from commercial vendors and used as received. NMR spectra were recorded on a Bruker 300 MHz or Varian UNITY INOVA 500 MHz spectrometer as indicated. Proton, fluorine, and carbon chemical shifts are reported in parts per million (ppm; δ) relative to tetramethylsilane or $CDCl_3$ solvent ($^1H$ δ 0, $^{19}F$ δ 0, $^{13}C$ δ 77.16, respectively). NMR data are reported as follows: chemical shifts, multiplicity (obs=obscured, app=apparent, br=broad, s=singlet, d=doublet, t=triplet, q=quartet, m=multiplet); coupling constant(s) in Hz; integration. Unless otherwise indicated, NMR data were collected at 25° C. Flash chromatography was performed using 40-60 um Silica Gel (60 Å mesh) on a Teledyne Isco Combiflash Rf system. Tandem liquid chromatography/mass spectrometry (LCMS) was performed on a Waters 2795 separations module and Waters 3100 mass detector. Analytical thin layer chromatography (TLC) was performed on EM Reagent 0.25 mm silica gel 60-F plates. Visualization was accomplished with UV light and aqueous potassium permanganate ($KMnO_4$) stain followed by heating. Liquid chromatography/mass spectrometry (LCMS) was performed on an Agilent 1290 Infinity separations module and 6230 time-of-flight (TOF) mass detector operating in ESI+ mode. Compound purity and identity were determined by UPLC-MS (Waters, Milford, Mass.). Purity was measured by UV absorbance at 210 nm. Identity was determined on a SQ mass spectrometer by positive electrospray ionization. Mobile Phase A consisted of either 0.1% ammonium hydroxide or 0.1% trifluoroacetic acid in water, while mobile Phase B consisted of the same additives in acetonitrile. The gradient ran from 5% to 95% mobile Phase B over 0.8 minutes at 0.45 ml/min. An Acquity BEH C18, 1.7 um, 1.0×50 mm column was used with column temperature maintained at 65° C. Compounds were dissolved in DMSO at a nominal concentration of 1 mg/mL, and 0.25 uL of this solution was injected.

Example 1A: Preparation of Ethyl 1-(3-chloro-4-hydroxybenzyl)-4-(2-phenoxyethyl)piperidine-4-carboxylate (1)

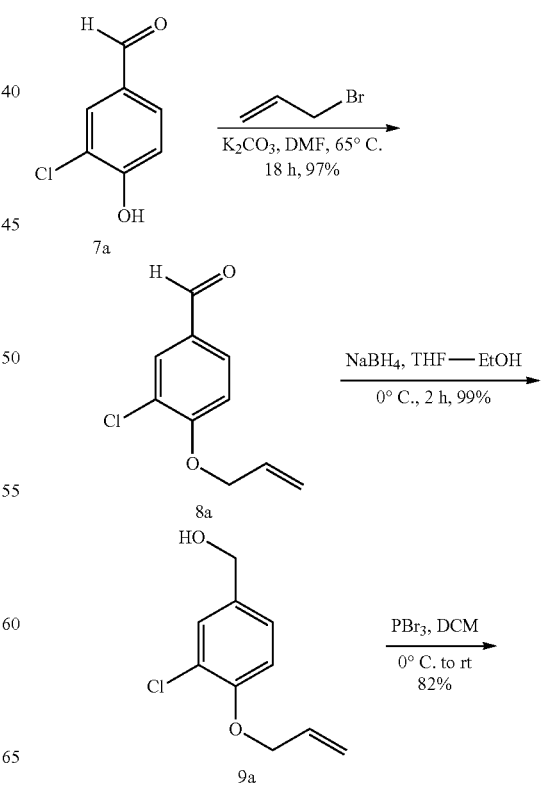

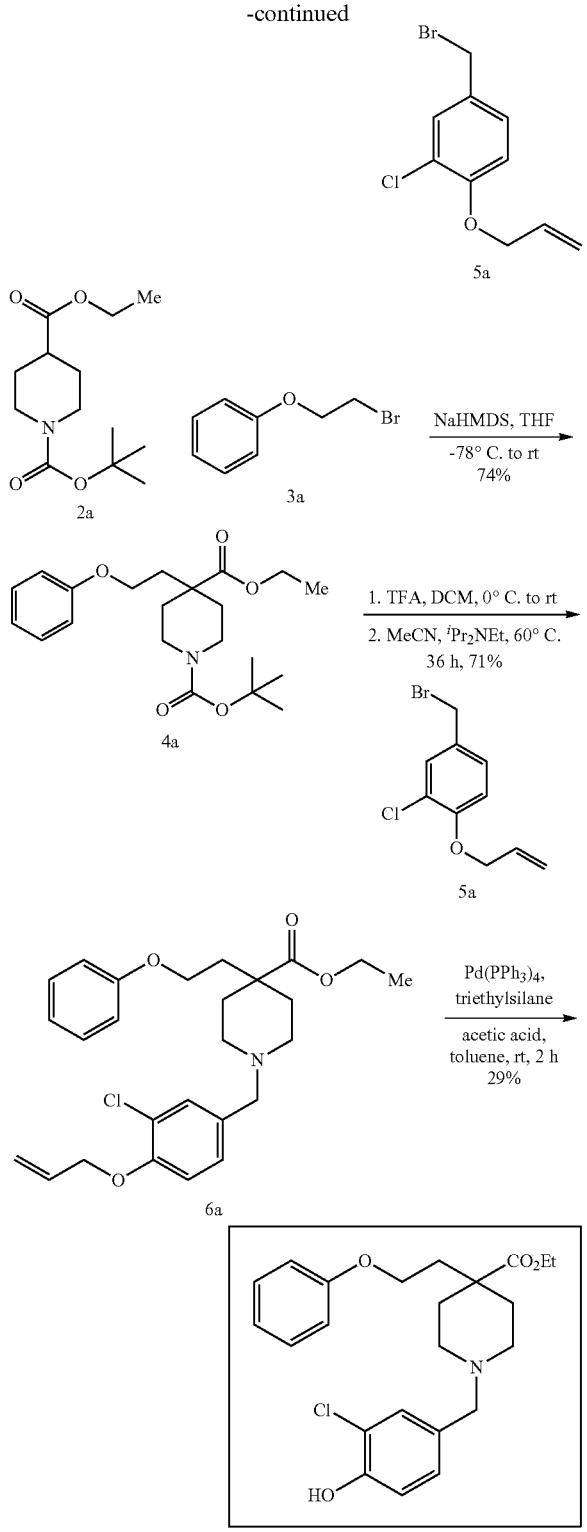

4-(allyloxy)-3-chlorobenzaldehyde (8a)

To a solution of 3-chloro-4-hydroxybenzaldehyde (7a, 5.0 g, 31.9 mmol) in anhydrous DMF (20 mL) at rt under nitrogen atmosphere was added $K_2CO_3$ (13.2 g, 96.0 mmol) in one portion followed by addition of allyl bromide (4.2 mL, 47.9 mmol). The mixture was stirred at 65° C. for 18 hr. The mixture was cooled down to rt followed by addition of water (100 mL). The mixture was extracted with ethyl acetate (3×80 mL). The combined organic layer was washed with brine (80 mL), dried over $Na_2SO_4$, filtered and concentrated under reduced pressure. The crude product was purified by column chromatography over 80 g of silica and eluted with ethyl acetate/hexane (0-30%) to provide the 4-(allyloxy)-3-chlorobenzaldehyde (6.1 g, 97% yield) as colorless oil. $^1$H NMR (300 MHz, $CDCl_3$): δ 9.84 (s, 1H), 7.91 (s, 1H), 7.76 (d, J=8.4 Hz, 1H), 7.03 (d, J=8.3 Hz, 1H), 6.07 (m, 1H), 5.53 (dd, J=17.1, 1.3 Hz, 1H), 5.35 (dd, J=17.0, 1.4 Hz, 1H), 4.71 (m, 2H). MS (ESI$^+$): 197.2 (M+H).

(4-(allyloxy)-3-chlorophenyl)methanol (9a)

To a solution of 4-(allyloxy)-3-chlorobenzaldehyde (8a, 4.7 g, 23.9 mmol) in THF and EtOH (10 mL/10 mL) at 0° C. was added sodium borohydride (0.9 g, 23.9 mmol). The mixture was stirred at 0° C. for 2 h. The reaction was quenched by slow addition of satd aq $NaHCO_3$ solution (80 mL) at 0° C. The mixture was extracted with ethyl acetate (3×60 mL). The combined organic layer was washed with water (50 mL), brine (80 mL), dried over $Na_2SO_4$, filtered and concentrated under reduced pressure. The crude oil was put under high vacuum for 1 h. The crude product was used in the next step without further purification. $^1$H NMR (300 MHz, $CDCl_3$): δ 7.35 (s, 1H), 7.16 (d, J=8.4 Hz, 1H), 6.88 (d, J=8.4 Hz, 1H), 6.06 (m, 1H), 5.46 (dd, J=17.1, 1.5 Hz, 1H), 5.31 (dd, J=17.0, 1.3 Hz, 1H), 4.61 (m, 2H), 4.56 (s, 2H), 2.25 (brs, 1H).

1-(allyloxy)-4-(bromomethyl)-2-chlorobenzene (5a)

To a solution of (4-(allyloxy)-3-chlorophenyl) methanol (9a, 4.8 g, 24.2 mmol) in anhydrous methylene chloride (40 mL) at 0° C. under nitrogen atmosphere was added $PBr_3$ (2.5 mL, 26.6 mmol) dropwise. The mixture was stirred at 0° C. for 30 min then at rt for 1 h. The reaction mixture was slowly poured into ice and was stirred for 30 min. The mixture was extracted with methylene chloride (3×50 mL). The combined organic layer was washed with brine (50 mL), dried over $Na_2SO_4$, filtered and concentrated under reduced pressure. The crude product was purified by column chromatography over 40 g of silica and eluted with ethyl acetate/hexane (0-20%) to provide the title compound (5.2 g, 82% yield) as yellow oil. $^1$H NMR (300 MHz, $CDCl_3$): δ 7.42 (d, J=2.20 Hz, 1H), 7.22 (dd, J=2.2, 8.5 Hz, 1H), 6.87 (d, J=8.5 Hz, 1H), 6.05 (m, 1H), 6.46 (dd, J=1.5, 17.3 Hz, 1H), 5.32 (J=1.4, 10.5 Hz, 1H), 4.62 (m, 2H), 4.41 (s, 2H). MS (ESI$^+$): 262.5 (M+H).

1-tert-butyl 4-ethyl 4-(2-phenoxyethyl)piperidine-1, 4-dicarboxylate (4a)

To a solution of 1-tert-butyl 4-ethyl piperidine-1,4-dicarboxylate (2a, 10.2 g, 39.6 mmol) in anhydrous THF (60 mL) at −78° C. under nitrogen atmosphere was added NaHMDS (1 M solution, 51.5 mL, 51.5 mmol) dropwise. The mixture was stirred at −78° C. for 10 min, warmed to rt for 10 min, and stirred at −78° C. for 20 minutes. 2-bromoethoxybenzene (3a, 9.56 g, 47.6 mmol) was added in one portion. The yellow solution was stirred at −78° C. for 30 min then warmed to rt. The mixture was stirred at rt for 16 h. The reaction was quenched by slow addition of satd aq $NH_4Cl$ solution (50 mL) and the mixture was then diluted with water (100 mL), extracted with ethyl acetate (3×80 mL). The combined organic layer was washed with brine (80 mL, dried over Na$_2$SO$_4$, filtered and concentrated under reduced pressure. The crude product was purified by column chromatography over 80 g of silica and eluted with ethyl acetate/hexane (0-20%) to provide the title compound (11.4 g, 74% yield) as yellow oil. $^1$H NMR (300 MHz, CDCl$_3$): δ 7.27 (m, 2H), 6.93 (m, 1H), 6.84 (m, 2H), 4.15 (m, 3H), 3.98 (t, J=6.6 Hz, 2H), 3.86 (m, 2H), 2.94 (m, 2H), 2.15 (m, 2H), 2.05 (m, 3H), 1.44 (s, 9H), 1.21 (t, J=7.1 Hz, 3H). MS (ESI$^+$): 278.2 (M+H−100).

Ethyl-1-(4-(allyloxy)-3-chlorobenzyl)-4-(2-phenoxyethyl)piperidine-4-carboxylate (6a)

To a solution of 1-tert-butyl 4-ethyl 4-(2-phenoxyethyl) piperidine-1,4-dicarboxylate (4a, 1.6 g, 4.33 mmol) in anhydrous methylene chloride (10 mL) at 0° C. under nitrogen atmosphere was added trifluoroacetic acid (1.5 mL, 26.5 mmol) dropwise. The mixture was stirred at 0° C. for 1 h then at rt for 1 h. The solvent was removed under reduced pressure and then evaporated with toluene (3×10 mL). The crude product was put under high vacuum pump for 1 h. The crude oil was used in the next step without further purification.

To a solution of piperidine carboxylate (1.2 g, 4.33 mmol) in anhydrous acetonitrile (20 mL) was added 1-(allyloxy)-4-(bromomethyl)-2-chlorobenzene (5a, 1.7 g, 6.50 mmol) and N,N-diisopropylethylamine (2.3 mL, 13.00 mmol). The mixture was stirred at 60° C. for 36 h. The mixture was cooled down to rt and was diluted with water (50 mL), extracted with ethyl acetate (3×40 mL). The combined organic layer was washed with brine (30 mL), dried over Na$_2$SO$_4$, filtered and concentrated under reduced pressure. The crude product was purified by column chromatography over 40 g of silica and eluted with ethyl acetate/hexane (10-100%) to provide the title compound (1.4 g, 71% yield) as yellow oil. $^1$H NMR (300 MHz, CDCl$_3$): δ 7.33 (d, J=1.9 Hz, 1H), 7.29 (m, 2H), 7.11 (d, J=8.3 Hz, 1H), 6.92 (t, J=7.3 Hz, 1H), 6.84 (m, 3H), 6.18-5.94 (m, 1H), 5.46 (d, J=17.3 Hz, 1H), 5.31 (d, J=10.5 Hz, 1H), 4.60 (d, J=5.0 Hz, 2H), 4.17 (q, J=7.1 Hz, 2H), 3.95 (t, J=6.8 Hz, 2H), 3.36 (s, 2H), 2.67 (s, 2H), 2.21 (d, J=13.5 Hz, 2H), 2.04 (t, J=6.8 Hz, 4H), 1.58 (m, 2H), 1.23 (t, J=7.1 Hz, 3H). MS (ESI$^+$): 458.3 (M+H).

Ethyl 1-(3-chloro-4-hydroxybenzyl)-4-(2-phenoxyethyl)piperidine-4-carboxylate (1)

To a solution of ethyl 1-(4-(allyloxy)-3-chlorobenzyl)-4-(2-phenoxyethyl)piperidine-4-carboxylate (6a, 0.20 g, 0.45 mmol) in anhydrous toluene (10 mL) at rt was degassed with nitrogen for 30 min and was added Pd(PPh$_3$)$_4$ (23 mg, 0.023 mmol), triethylsilane (0.36 mL, 2.252 mmol) and acetic acid (0.129 mL, 2.252 mmol) was added. The mixture was stirred at rt for 2 h. The mixture was diluted with ethyl acetate (30 mL), washed with satd aq NaHCO$_3$ solution (30 mL), extracted with ethyl acetate (2×30 mL). The combined organic layer was washed with brine (30 mL), dried over Na$_2$SO$_4$, filtered and concentrated under reduced pressure. The crude product was purified by column chromatography over 12 g of silica and eluted with methanol/dichloromethane (0-20%) to provide the title compound (52 mg, 29% yield) as off-white solid. $^1$H NMR (300 MHz, CDCl$_3$): δ 7.28-7.23 (m, 3H), 7.09-7.06 (m, 1H), 6.96-6.78 (m, 4H), 4.21-4.09 (m, 2H), 3.95 (t, J=6.7 Hz, 2H), 3.41 (s, 2H), 2.87-2.77 (m, 2H), 2.25-2.02 (m, 6H), 1.66-1.59 (m, 2H), 1.23 (t, J=7.1 Hz, 3H). HRMS (ESI$^+$): calculated for C$_{23}$H$_{28}$ClNO$_4$ [M+H] 418.1785, found 418.1781.

Example 1B: Preparation of Isopropyl 1-(3-chloro-4-hydroxybenzyl)-4-(2-phenoxyethyl)piperidine-4-carboxylate (11a)

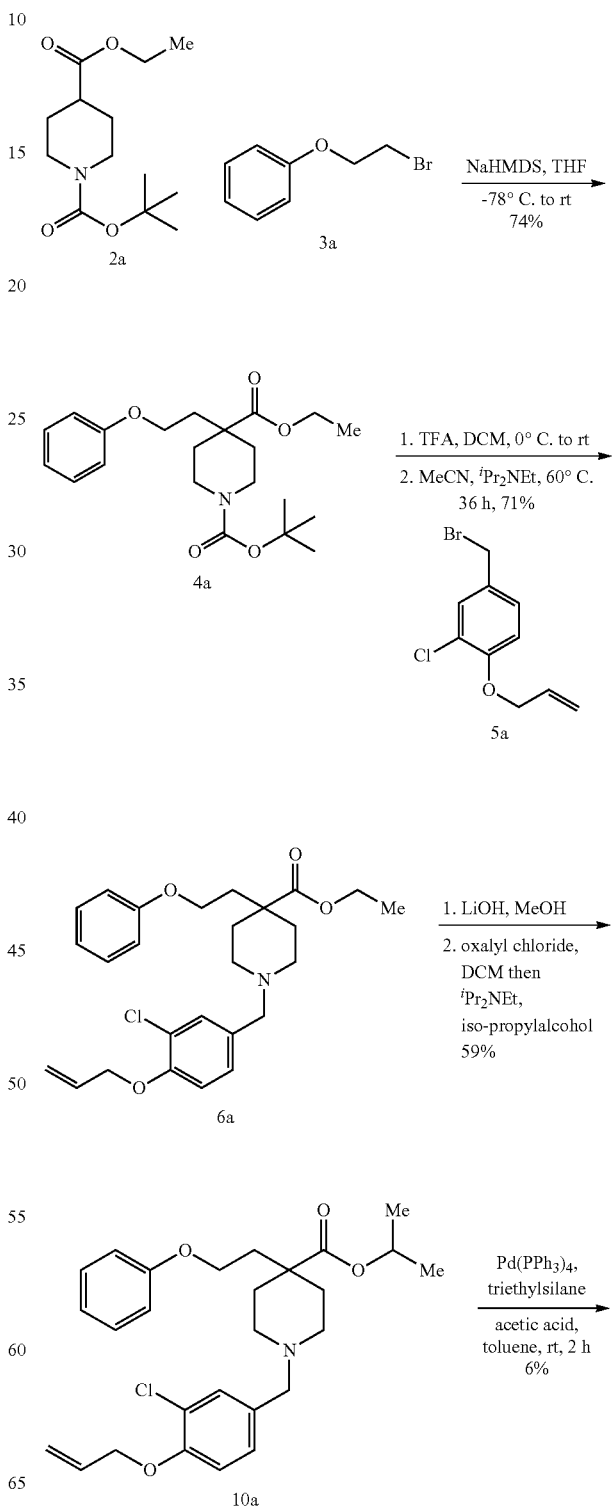

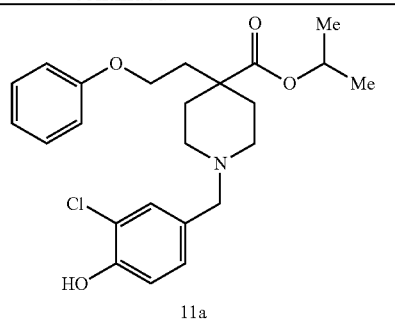

Iso-propyl 1-(4-(allyloxy)-3-chlorobenzyl)-4-(2-phenoxyethyl)piperidine-4-carboxylate (10a)

To a solution of ethyl 1-(4-(allyloxy)-3-chlorobenzyl)-4-(2-phenoxyethyl)piperidine-4-carboxylate (6a, 1.1 g, 2.4 mmol) in MeOH (15 mL) was added LiOH (0.58 g, 24.02 mmol) in water (1.5 ml) at rt. The mixture was stirred at rt for 48 h. The reaction mixture was then diluted with water and extracted with ethyl acetate. The combined organic layer was washed with brine and dried over $Na_2SO_4$ and concentrated under reduced pressure. The crude product mixture was used in the next step without further purification.

To a solution of crude 1-(4-(allyloxy)-3-chlorobenzyl)-4-(2-phenoxyethyl)piperidine-4-carboxylic acid (0.2 g, 0.47 mmol) in anhydrous DCM (5 ml) at 0° C. under nitrogen atmosphere was added oxalyl chloride (0.08 ml, 0.93 mmol. The mixture was stirred at 0° C. for 30 minutes and then at rt for 3 h. The solvent was then evaporated and the crude product mixture was dissolved in DCM (5 ml) at 0° C. under nitrogen atmosphere. DIPEA (0.24 ml, 1.4 mmol) was added drop wise and then isopropyl alcohol (0.06, 0.93 mmol) was added in one portion. The mixture was stirred at 0° C. for 4 h. The reaction was quenched with saturated aqueous NaHCO3 solution and extracted with ethyl acetate. The combined organic layer was washed with brine, dried over $Na_2SO_4$, filtered and concentrated under reduced pressure. The crude product was purified by column chromatography over 12 g of silica and eluted with hexane/ethyl acetate (0-100%) to provide the title compound (0.13 g, 59.2% yield). $^1$H NMR (300 MHz, DMSO): δ 7.38 (m, 1H), 7.24 (m, 3H), 7.07 (m, 1H), 6.88 (m, 3H), 6.02 (m, 1H), 5.40 (m, 1H), 5.26 (m, 1H), 4.62 (d, J=5.0 Hz, 2H), 3.93 (t, J=6.5 Hz, 4H), 3.52 (s, 4H), 2.71 (m, 2H), 2.20 (m, 2H), 2.03 (m, 2H), 1.91 (m, 2H), 1.51 (m, 2H). LCMS (ESI$^+$): 430.3 (M+H).

Isopropyl 1-(3-chloro-4-hydroxybenzyl)-4-(2-phenoxyethyl)piperidine-4-carboxylate (11a)

To a solution of iso-propyl 1-(4-(allyloxy)-3-chlorobenzyl)-4-(2-phenoxyethyl)piperidine-4-carboxylate (7a, 0.13 g, 0.275 mmol) in anhydrous toluene (6 mL) at rt was degassed with nitrogen for 30 min and was added Pd(PPh$_3$)$_4$ (14 mg, 0.014 mmol), triethylsilane (0.22 mL, 1.377 mmol) and acetic acid (0.079 mL, 1.377 mmol) was added. The mixture was stirred at rt for 2 h. The mixture was diluted with ethyl acetate (30 mL), washed with satd aq NaHCO$_3$ solution (30 mL), extracted with ethyl acetate (2×30 mL). The combined organic layer was washed with brine (30 mL), dried over $Na_2SO_4$ and concentrated under reduced pressure. The crude product was purified by column chromatography over 12 g of silica and eluted with methanol/dichloromethane (0-10%) to provide the title compound (7.45 mg, 6.26% yield). $^1$H NMR (300 MHz, CDCl$_3$): δ 7.31-7.20 (m, 3H), 7.09-7.05 (m, 1H), 6.98-6.86 (m, 2H), 6.82 (m, 2H), 5.13-4.97 (m, 1H), 3.95 (t, J=6.8 Hz, 2H), 3.41 (s, 2H), 2.80-2.76 (m, 2H), 2.28-2.06 (m, 4H), 2.07-1.96 (m, 3H), 1.66-1.58 (m, 2H), 1.22 (d, J=6.3 Hz, 6H). LCMS (ESI$^+$): 431.9 (M+).

Example 1C: Preparation of Tert-butyl 1-(3-chloro-4-hydroxybenzyl)-4-(2-phenoxyethyl)piperidine-4-carboxylate (12a)

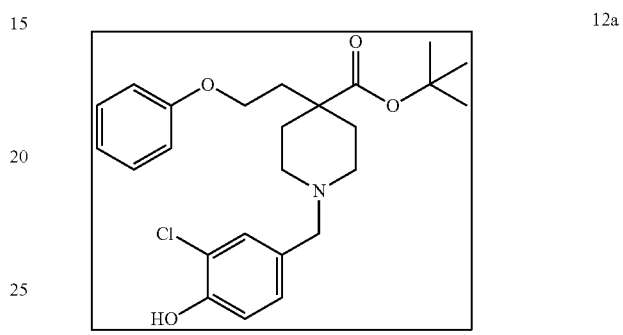

This compound was prepared similarly to compound 11a by following the procedures in Example 1B replacing iso-propylalcohol with tert-butyl alcohol in the reaction of compound 6a. $^1$H NMR (300 MHz, CDCl$_3$): δ 7.30-7.23 (m, 3H), 7.11-7.08 (m, 1H), 6.96-6.890 (m, 2H), 6.88-6.82 (m, 2H), 3.96 (t, J=7.2 Hz, 2H), 3.36 (s, 2H), 2.71-2.67 (m, 2H), 2.21-1.94 (m, 7H), 1.62-1.48 (m, 2H), 1.46 (s, 9H). LCMS (ESI$^+$): 446.2 (M+H).

Example 2: Assay of Thiol Isomerase Activity

PDI inhibitors were evaluated in an insulin turbidimetric assay to assess their ability to block the reductase activity of PDI. The assay measured the aggregation of insulin chains by monitoring absorbance at 650 nM as previously described in Jasuja, R. et al. Protein disulfide isomerase inhibitors constitute a new class of antithrombotic agents. *J Clin Invest* 122, 2104-2113 (2012) (hereinafter "Jasija"). Cleavage of disulfide bonds within insulin by PDI results in aggregation of insulin. When PDI is inhibited, there is a decrease in aggregation of insulin, and therefore a decrease in absorbance signal at 650 nm. Recombinant human PDI expressed and purified from *E. coli*., mixed with bovine insulin (Sigma), and added to assay plates. The reaction mixture for insulin reduction assays contained 100 mM potassium phosphate, pH 7.4; 0.75 mM DTT, 2 mM EDTA, 0.1 mM bovine insulin, and 0.8 μM purified human PDI in a total volume of 135 μl in a 96 well plate. The progress of the reaction was monitored for 30 min at 23° C. Indicated inhibitors or control buffer was added prior to the addition of enzyme at the concentrations indicated. PDI activity in the presence of compound was determined by the formula, PDI activity (%)={OD$_{(compound+PDI+DTT)}$−OD$_{(DTT)}$}/{OD$_{(PDI+DTT)}$−OD$_{(DTT)}$}×100

% enzyme inhibition={1−OD$_{max(compound+enzyme)}$/OD$_{max(buffer\ control+enzyme)}$}

IC$_{50}$ values were calculated using non-linear regression analysis. IC$_{50}$ values for compounds shown in the invention are shown in Tables A, B, and C. FIG. 1 shows enzymatic activity in % inhibition of Compound 1 over the log of the concentration of the inhibitor.

The insulin turbidimetric assay was used with alternative thiol isomerases to evaluate the specificity of inhibitors, as shown in Tables B and C. Other oxidoreductases used to evaluate the specificity of inhibitors include ERp5, thioredoxin (TR), and thioredoxin reductase (TRR). As can be seen from the data in Tables B and C, the compounds of the invention are highly selective for PDI.

Example 3: Testing the Stability of PDI Inhibitors

The stability of PDI inhibitors was measured in the presence of PBS pH 7.4 with 1% DMSO. PDI inhibitors were added to plasma (in triplicate at 1 µM) on six separate plates and allowed to equilibrate at room temperature for 48 hours. At each time point (0, 2, 4, 8, 24, and 48 hours), one

TABLE C

Structure activity relationships showing improved mouse plasma stability and inhibition of platelet aggression by analogs of Compound 1.

| Structure | IC$_{50}$ | Specif. (ERp5, TR, TRR)* | Plasma stability human | Plasma stability mouse | Platelet Aggregation |
|---|---|---|---|---|---|
| (Compound with CO$_2$Et) | 0.3-0.6 µM | >30 µM | 100% | 5.3% | 25-50% |
| (Compound with isopropyl ester) | 0.85 µM | >30 µM | 97.9% | 75.3% | 97% |
| (Compound with tert-butyl ester) | 0.65 µM | >30 µM | 98.7% | 95.6% | 100% |
| (Compound with CO$_2$Et and amide) | 2.25 µM | >30 µM | 100% | 100% | 100% |

*ERp5 is Endoplamsic Reticulum protein 5, TR is thiorededoxin; TRR is thioredoxin reductase plate was removed and an aliquot was taken out from each well and analyzed by UPLC-MS.

Example 4: Platelet Aggregation

Platelet Rich Plasma (PRP) was prepared from whole blood obtained from individual donors and drawn into Acid Citrate Dextrose (ACD) at 15% of total volume. PGE-1 was added to a final concentration of 0.15 μM to maintain the resting state. PRP was spun at 1000 g×10 minutes and the supernatant was discarded. The platelet pellet was resuspended in Modified HEPES-Tyrodes buffer pH 7.3. The 1× washed platelets were incubated for 20 minutes at 37° C. until they were in a quiescent state. The above washing procedure was then repeated. The 2× washed platelets were allowed to rest for 20 minutes at 37° C. Platelets were then counted and the concentration of platelets in suspension was adjusted to 200,000 platelets/μL. The 2× washed platelets were treated with compounds at 30 μM, and were incubated for 30 minutes at 37° C. Following incubation, platelets were added to a cuvette and stirred at 37° C. in a Chrono-Log Platelet Aggregometer. In order to initiate aggregation, a concentration of SFLLRN, the thrombin receptor activating peptide, sufficient to elicit 60-70% light transmittance was added to the cuvette. Therefore, a range of 2-3 μM SFLLRN was used in order to accommodate small differences in sensitivity to SFLLRN between individual donors. Prior to reading, the aggregometer was scaled so that unstimulated, washed platelets are set to 0% light transmittance, and buffer alone with no platelets is set to 100% light transmittance. The light transmittance of each sample was recorded as a measure of aggregation. Data were recorded as a single point representing maximum aggregation in the presence of compound and were compared to samples exposed to vehicle (DMSO) alone. See Jasuja Example 5: Thrombus Formation Intravital Microscopy.

Intravital video microscopy, laser injury, and image analysis was performed as previously described in Jasuja. Intravital video microscopy of the cremaster muscle microcirculation was performed as previously described. Digital images were captured with a Cooke Sensicam CCD camera (The Cooke Corporation) connected to a VS4-1845 Image Intensifier GEN III (Video Scope International).

Laser-Induced Injury.

Injury to a cremaster arteriolar (30-50 μm diameter) vessel wall was induced with a Micropoint Laser System (Photonics Instruments) focused through the microscope objective, parfocal with the focal plane and tuned to 440 nm through the dye cell containing 5 mM coumarin in methanol. Platelet-specific anti-CD42b antibody conjugated to Dylight 649 (0.1 μg/g body weight) were infused into the mouse for visualization of thrombus formation. Data were captured digitally from two fluorescence channels, 488/520 nm and 647/670 nm. Data acquisition was initiated both prior to and following a single laser pulse for each injury. The microscope system was controlled and images were analyzed using Slidebook (Intelligent Imaging Innovations).

Image Analysis.

For each thrombus generated by laser injury, a rectangular mask was defined that included a portion of the vessel upstream of the site of injury. The maximum fluorescence intensity of the pixels contained in this mask was extracted for all frames (pre- and post-injury) for each thrombus. The mean value calculated from the maximal intensity values in the mask for each frame was determined and used as the background value. Finally, for each frame the integrated fluorescence intensity was calculated as per following equation:

$$\begin{matrix}\text{Integrated} \\ \text{fluorescence} \\ \text{intensity}\end{matrix} = \begin{matrix}\text{Sum} \\ \text{intensity} \\ \text{of signal}\end{matrix} - \left(\begin{matrix}\text{mean of the maximal} \\ \text{background intensity}\end{matrix} \times \begin{matrix}\text{area of the} \\ \text{signal}\end{matrix}\right)$$

This calculation was performed for all frames in each thrombus and plotted versus time to provide the kinetics of thrombus formation. For multiple fluorescence channels, calculations of background were made independently for each channel. The data from 25-30 thrombi were used to determine the median value of the integrated fluorescence intensity to account for the variability of thrombus formation at any given set of experimental conditions.

All publications and patents cited herein are hereby incorporated by reference in their entirety.

Those skilled in the art will recognize, or be able to ascertain using no more than routine experimentation, many equivalents to the specific embodiments of the invention described herein. Such equivalents are intended to be encompassed by the following claims.

The invention claimed is:
1. A method for treating acute myocardial infarction, transient ischemic attacks, peripheral vascular disease, pulmonary embolism, or deep vein thrombosis in a patient, comprising administering to the patient a compound of Formula (I):

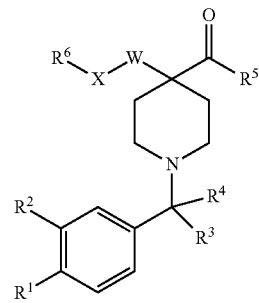

Formula (I)

or a pharmaceutically acceptable salt thereof, and a pharmaceutically acceptable excipient or solvent, wherein:
$R^1$ is OH or acyloxy;
$R^2$ is selected from H, lower alkyl, and halogen;
$R^3$ and $R^4$ are independently selected from H, F, and alkyl, or $R^3$ and $R^4$ taken together with the carbon atom to which they are attached form a carbonyl group or a substituted or unsubstituted 3-7 membered cycloalkyl ring;
$R^5$ is $OR^7$, or $NR^7R^8$, wherein $R^7$ and $R^8$ are each independently selected from H and substituted or unsubstituted alkyl, aryl, aralkyl, cycloalkyl, and cycloalkylalkyl, or taken together with the nitrogen atom to which they are attached form a substituted or unsubstituted 3-7 membered heterocyclyl ring;
W represents a $C_1$-$C_3$ alkylene group;
X is selected from O, S, and $NR^9$, wherein $R^9$ is H or lower alkyl; and $R^6$ is substituted or unsubstituted aryl or substituted or unsubstituted heteroaryl.

2. The method according to claim 1, wherein $R^1$ is OH.

3. The method according to claim 1, wherein $R^2$ is H or Cl.

4. The method according to claim 1, wherein $R^3$ and $R^4$ are H, or $R^3$ and $R^4$ taken together with the carbon atom to which they are attached form a carbonyl group.

5. The method according to claim 1, wherein $R^5$ is $OR^7$, wherein $R^7$ is substituted or unsubstituted alkyl.

6. The method according to claim 1, wherein W is ethylene.

7. The method according to claim 1, wherein X is O.

8. The method according to claim 1, wherein $R^6$ is substituted or unsubstituted aryl.

9. The method according to claim 1, wherein the compound is a compound having a structure selected from:

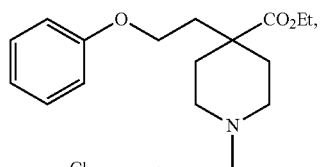

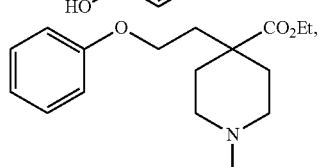

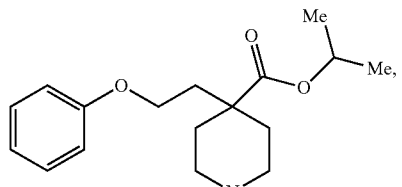

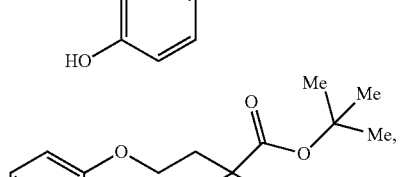

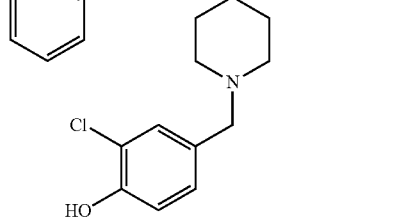

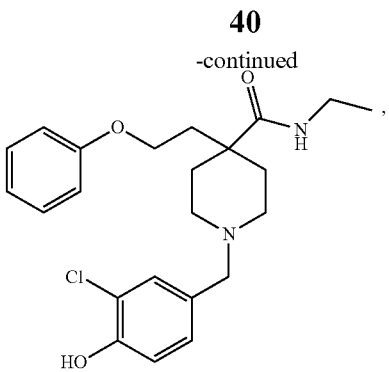

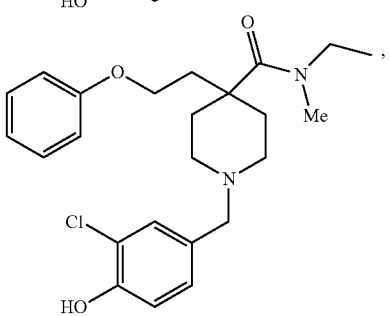

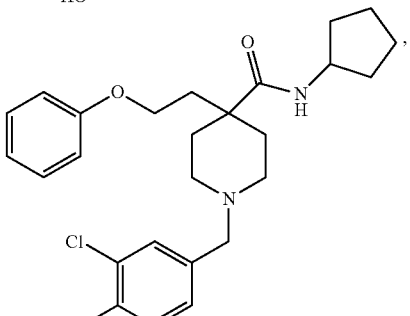

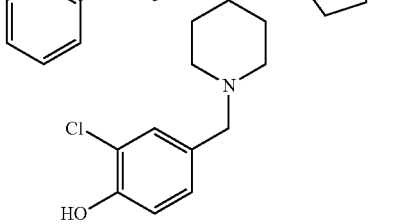

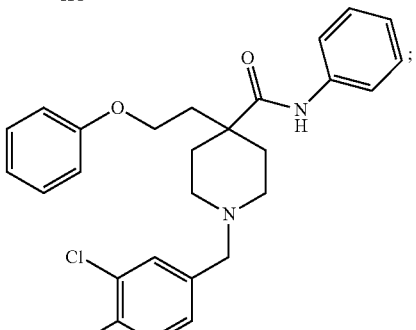

or a pharmaceutically acceptable salt thereof.

10. A method for inhibiting protein disulfide isomerase in a cell, comprising contacting the cell with a compound of Formula (I):

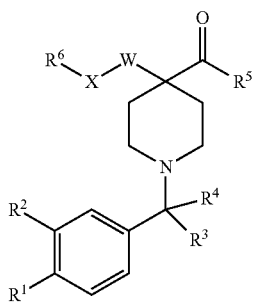

Formula (I)

or a pharmaceutically acceptable salt thereof, and a pharmaceutically acceptable excipient or solvent, wherein:

$R^1$ is OH or acyloxy;

$R^2$ is selected from H, lower alkyl, and halogen;

$R^3$ and $R^4$ are independently selected from H, F, and alkyl, or $R^3$ and $R^4$ taken together with the carbon atom to which they are attached form a carbonyl group or a substituted or unsubstituted 3-7 membered cycloalkyl ring;

$R^5$ is $OR^7$, or $NR^7R^8$, wherein $R^7$ and $R^8$ are each independently selected from H and substituted or unsubstituted alkyl, aryl, aralkyl, cycloalkyl, and cycloalkylalkyl, or taken together with the nitrogen atom to which they are attached form a substituted or unsubstituted 3-7 membered heterocyclyl ring;

W represents a $C_1$-$C_3$ alkylene group;

X is selected from O, S, and $NR^9$, wherein $R^9$ is selected from H or lower alkyl; and $R^6$ is substituted or unsubstituted aryl or substituted or unsubstituted heteroaryl.

11. The method according to claim 10, wherein $R^1$ is OH.

12. The method according to claim 10, wherein $R^2$ is H or Cl.

13. The method according to claim 10, wherein $R^3$ and $R^4$ are H, or $R^3$ and $R^4$ taken together with the carbon atom to which they are attached form a carbonyl group.

14. The method according to claim 10, wherein $R^5$ is $OR^7$, wherein $R^7$ is substituted or unsubstituted alkyl.

15. The method according to claim 10, wherein W is ethylene.

16. The method according to claim 10, wherein X is O.

17. The method according to claim 10, wherein $R^6$ is substituted or unsubstituted aryl.

18. The method according to claim 10, wherein the compound is a compound having a structure selected from:

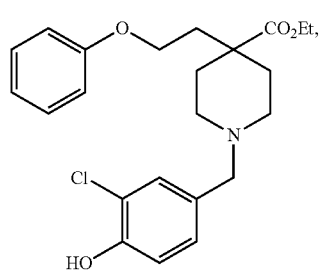

-continued

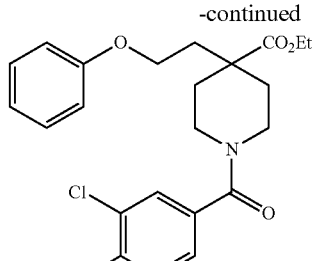

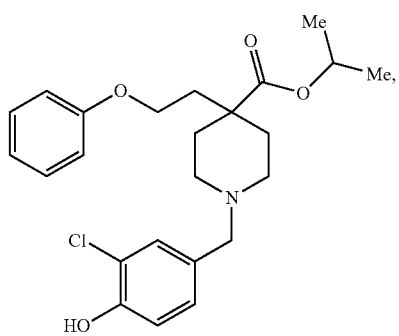

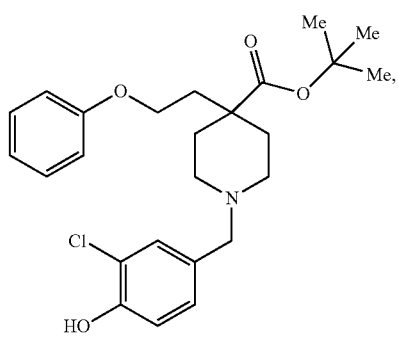

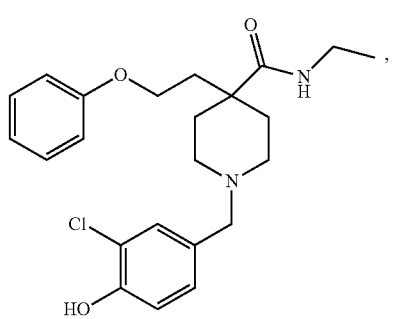

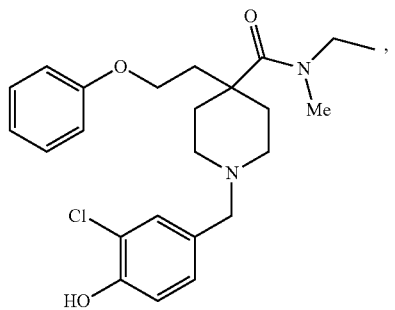

-continued
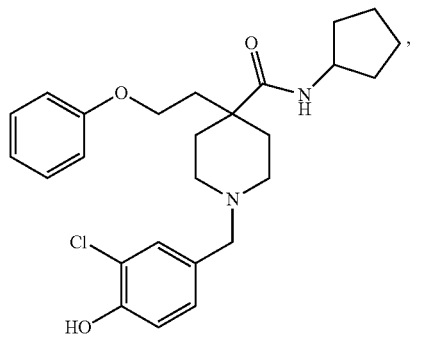
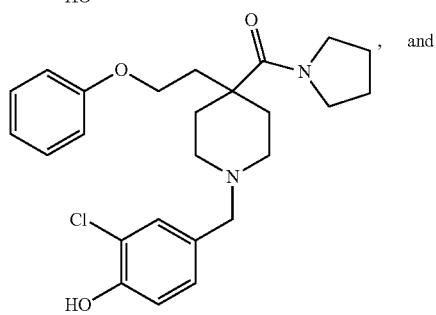
and
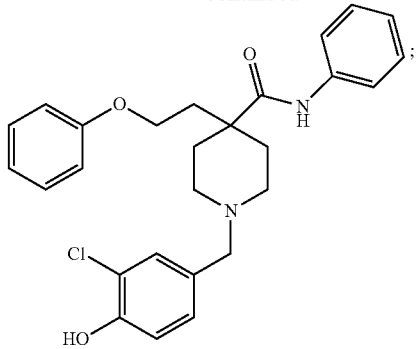
or a pharmaceutically acceptable salt thereof.
* * * * *